United States Patent [19]

Kilpper et al.

[11] 4,419,519

[45] Dec. 6, 1983

[54] CONTINUOUS PREPARATION OF PHTHALIMIDE

[75] Inventors: Gerhard Kilpper, Battenberg; Johannes Grimmer, Ludwigshafen, both of Fed. Rep. of Germany

[73] Assignee: BASF Aktiengesellschaft, Fed. Rep. of Germany

[21] Appl. No.: 278,697

[22] Filed: Jun. 29, 1981

Related U.S. Application Data

[63] Continuation of Ser. No. 119,958, Feb. 8, 1980.

[30] Foreign Application Priority Data

Mar. 22, 1979 [DE] Fed. Rep. of Germany ....... 2911245

[51] Int. Cl.$^3$ ............................................. C07D 209/48
[52] U.S. Cl. .................................................. 548/480
[58] Field of Search ...................... 260/326 R; 548/480

[56] References Cited

U.S. PATENT DOCUMENTS

| B 486,678 | 3/1976 | Hetzel et al. .................... 260/326 R |
| 1,966,068 | 7/1934 | Jaeger et al. ......................... 260/124 |
| 2,566,992 | 9/1951 | Morgan et al. ................. 260/326 R |
| 2,668,326 | 2/1954 | Schlaudocker ....................... 18/47.2 |
| 4,001,273 | 1/1977 | Hetzel et al. .................... 260/326 R |

FOREIGN PATENT DOCUMENTS

| 85380 | 9/1921 | Austria . |
| 2056891 | 5/1972 | Fed. Rep. of Germany . |
| 1465511 | 2/1977 | United Kingdom . |

OTHER PUBLICATIONS

Ullmans Encyklopadie der Technischen Chemie, vol. 13, p. 735.

Primary Examiner—Donald G. Daus
Assistant Examiner—M. C. Eakin
Attorney, Agent, or Firm—Keil & Witherspoon

[57] ABSTRACT

A process for the continuous preparation of phthalimide by reacting phthalic anhydride with ammonia in about the stoichiometric ratio, in a mixing apparatus and subsequently in a reaction tube at a particular flow velocity and a particular temperature.

The phthalimide obtainable by the process of the invention is a valuable starting material for the preparation of dyes, pesticides and pigments, especially copper phthalocyanines.

11 Claims, No Drawings

CONTINUOUS PREPARATION OF PHTHALIMIDE

This is a continuation, of application Ser. No. 119,958, filed Feb. 8, 1980.

The invention relates to a process for the continuous preparation of phthalimide by reacting phthalic anhydride with ammonia in about the stoichiometric ratio, in a mixing apparatus and subsequently in a reaction tube at a particular flow velocity and a particular temperature.

U.S. Pat. No. 1,966,068 discloses the batchwise preparation of phthalimide by passing ammonia into a melt of phthalic anhydride and subliming the end product formed; it is recommended to use a large excess of ammonia, particularly where crude phthalic anhydride is employed as the starting material. Other batchwise methods of carrying out the reaction are described in Austrian Patent No. 85,380 and U.S. Pat. No. 2,668,326. All these processes have the disadvantage that they are operated batchwise. The reaction temperature can only be raised slowly since otherwise substantial amounts of unconverted phthalic anhydride, for example a total of from 5 to 50 percent by weight of the total anhydride starting material, sublime together with the phthalimide. To achieve substantially complete conversion the processes must be carried out with a large excess of ammonia, for example with from 4 to 8 times the stoichiometric amount of ammonia, based on phthalic anhydride. The reaction at first produces one mole of steam per mole of ammonia; during this first stage of the reaction, the steam entrains pure phthalic anhydride in the off-gas. Thereafter, phthalimide is also entrained, to an extent which progressively increases with the degree of conversion. Phthalic anhydride, and the monoammonium phthalate formed during the reaction, may, at relatively high conversion and relatively high concentration of by-products in the off-gas, deposit on the walls of the apparatus and cause blockages of pipes and valves.

U.S. Pat. No. 2,668,326 discloses a process wherein phthalic anhydride and ammonia are reacted batchwise and the off-gases from the reaction are washed with water or with a high-boiling hydrocarbon as a solvent. The wash liquid is advantageously recycled, causing the suspended phthalimide to accumulate. This suspension is also used to cool and quench the hot reaction mixture.

German Laid-Open Application DOS No. 2,056,891 describes a continuous process wherein the two starting materials flow in co-current. A melt of phthalic anhydride and excess ammonia is introduced into the top of a vertical reaction tube heated to 200°-300° C., and the phthalimide which forms is taken off at the bottom. The reaction mixture enters a sublimation chamber where phthalimide is precipitated by cooling; the non-condensed part of the phthalimide, phthalic anhydride, by-products, ammonia and steam are removed via a gas baffle. An essential feature of the process of the said DOS is that ammonia is used in an excess of at least 20 percent, preferably of from 25 to 35 percent by weight; the space-time yield is 0.98 part per hour per liter of reactor space.

In all these cases, there is still some phthalic anhydride present in the off-gas; its amount is at least in excess of 5 percent by weight, but often in excess of 20 percent by weight, of the off-gas, which is unsatisfactory, particularly in industrial operation. In the continuous process, the off-gas in general contains, in addition to steam, from 5 to 35 percent by weight of phthalic anhydride, from 20 to 40 percent by weight of phthalimide and from 3 to 10 percent by weight of ammonia, based on the total amount of off-gas. In these conventional processes, there are, in some cases, substantial losses of end product, the amount lost depending on the reaction conditions, temperature and composition of the reaction mixture.

In the process described in German Laid-Open Application DOS 2,056,891, an attempt is made to minimize the loss by passing the off-gases through a receiver fitted with gas baffles, which, through deflecting the stream of off-gas, whilst the receiver is being cooled, cause part of the entrained phthalic anhydride and phthalimide vapor to deposit. According to the process described in U.S. Pat. No. 2,668,326, the vapors containing phthalic anhydride and phthalimide are passed through a water-operated scrubber in which the steam is condensed and the organic compounds crystallize out. The resulting slurry is used as a liquid for quenching the hot phthalimide melt. A disadvantage of this process is that the operations of isolating the solid phthalimide from the aqueous phase by filtration or centrifuging and drying are involved. In every case, the phthalimide is contaminated with phthalic anhydride and must be purified, for example by fractional sublimation.

German Laid-Open Application DOS Nos. 2,334,379 and 2,334,916 disclose that phthalimide can be prepared continuously be reacting ammonia and phthalic anhydride at an elevated temperature in counter-current, using a molar ratio of from 0.9:1 to 1.1:1. The off-gas formed in the reaction is advantageously washed with aqueous ammonia. Whilst, in the batchwise and continuous processes mentioned earlier, in general from 20 to 40 percent by weight of phthalimide, based on the amount by weight of off-gas, are lost with the off-gas when the process is operated industrially, the off-gas of the two last-mentioned processes contains less than 0.5 percent by weight of phthalimide even without a wash with aqueous ammonia, and less than 0.001 percent by weight of phthalimide if such a wash is used. Reactors which may be used are stirred kettle cascades, advantageously comprising from 3 to 6 stirred kettles arranged in series, or columns of which a part serves as a stirred kettle and of which the lower part is so equipped that the reactants react with one another with minimal back-mixing. For example, tray columns or bubblers, in which the lower part is filled with packing, are employed. It is also possible to use a stirred vessel with downstream counter-current column. Advantageously, tray columns are used. Suitable temperatures are not less than 150° C., especially from 150° to 210° C., at the top, and not more than 270° C., in particular from 240° to 265° C., at the bottom of the column, with the temperature increasing progressively from top to bottom. The ammonia throughput is advantageously from 90 to 280, preferably from 160 to 230 kg/h per square meter of reactor cross-section. Advantageously, two starting materials are reacted with one another in counter-current in a column in the above-mentioned manner, at the said reaction temperature. The reaction mixture, substantially consisting of phthalimide, is taken off as a melt at the bottom of the column, whilst the off-gas issues at the top of the column.

In general, the off-gas from the above counter-current process contains from 40 to 60 percent by weight of steam, from 0.3 to 1 percent by weight of ammonia and from 35 to 50 percent by weight of phthalic anhydride and, depending on the reaction temperature, from 0 to 6 percent by weight of phthalic acid, from 0.3 to 1 percent by weight of phthalimide, from 0 to 8 percent by weight of monoammonium phthalate and from 0 to 10 percent weight of diammonium phthalate.

German Laid-Open Application DOS No. 2,334,916 discloses that the off-gas from the reaction is scrubbed with a melt, which contains not less than 70 percent by weight of phthalimide, at not less than 210° C., after which the melt can be recycled to the reaction. After the scrubbing, the off-gas contains not more than 1.5, and in most cases less than 0.3, percent by weight of phthalic anhydride and jot more than 70a in most cases less than 65, percent by weight of phthalimide. The off-gas has thus been substantially freed from by-products and the proportion of phthalimide has been increased. Since the off-gas is advantageously trapped in aqueous alkali, eg. in sodium hydroxide or potassium hydroxide solution of from 5 to 20 percent strength by weight, in which phthalimide dissolves, the resulting solutions can, for example, be employed directly as starting materials for the synthesis of anthranilic acid and isatoic anhydride by reaction of an alkali metal phthalimidate with an alkali metal hypochlorite. On the other hand, even a small proportion of phthalic anhydride present would also dissolve in alkali and would cause the subsequent synthesis to result in impure end products, necessitating expensive and involved purification operations entailing losses of end products.

We have found that phthalimide can advantageously be prepared continuously by reacting phthalic anhydride with ammonia at an elevated temperature if (a) phthalic anhydride in the molten state is mixed, and reacted, with ammonia, using a ratio of from 1 to 1.1 moles of the latter per mole of the former, in a mixing apparatus at from 135° to 300° C. under a pressure of at most 50 bar, thereafter (b) the resulting mixture is reacted in a reaction tube at a flow velocity greater than 0.01 meter per second, at from 235° to 300° C. under a pressure of at most 50 bar and (c) phthalimide is isolated in a conventional manner from the reaction mixture which issues.

The reaction can be represented by the following equation:

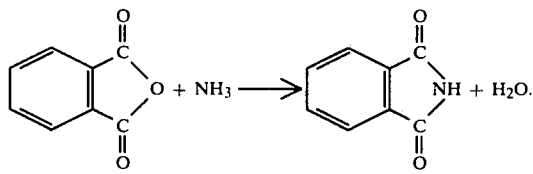

Compared to the conventional batchwise processes, the process according to the invention gives phthalimide more simply and more economically, with better space-time yield and in higher purity. The process according to the invention is also simpler and more economical than the continuous process described in German Laid-Open Application DOS No. 2,056,891, since, surprisingly, a substantial excess of ammonia is not required; furthermore, there is a higher yield of pure end product, since less phthalic anhydride, in general less than 0.5 percent by weight, virtually no monoammonium phthalate and no diammonium phthalate are present as by-products in the end product obtained. Complicated purification equipment, the use of a gas baffle and special working up of the end product are unnecessary.

The end product prepared according to the invention is thus of particular importance as an intermediate in the industrial preparation of anthranilic acid and isatoic anhydride; advantageously, the phthalimide is dissolved directly, ie. without intermediate isolation, in dilute sodium hydroxide solution, and the resulting solution is subjected to a Hofmann degradation with hypochlorite solution. Particularly in the case of a Hofmann degradation it is necessary to employ a phthalimide solution which contains virtually no free ammonia, since the latter can form explosive chlorine-nitrogen compounds with hypochlorite solutions: hence, the fact that a substantial excess of ammonia is not needed for the process of preparation according to the invention is an advantage. The end product, obtained as a liquid, can, without further purification, be directly worked up to give anthranilic acid or isatoic anhydride, or be isolated as a solid by using a cooling drum.

Compared to the processes described in German Laid-Open Application DOS Nos. 2,334,379 and DOS 2,334,916, the process according to the present invention is simpler and more economical and gives a higher space-time yield if the overall production process, including working up the end product, is considered. The process requires only a minimum of measuring and regulating equipment, which additionally improves the reliability of operation. If the published Examples of the conventional continuous processes are considered, it is seen that the throughputs achieved, in kilograms per hour per square meter of reactor cross-section, are 1,885 in the case of German Laid-Open Application DOS No. 2,056,891, from 800 to 3,000 in the case of German Laid-Open Application DOS No. 2,334,379 and again from 800 to 3,000 in the case of German Laid-Open Application DOS No. 2,334,916. In the process according to the invention, the throughputs used are in excess of 10,000 kilograms per hour per square meter of reactor cross-section and plant can be put into operation more rapidly. All these advantageous results are surprising in view of the prior art.

The reaction according to the invention is carried out with a ratio of from 1 to 1.1, preferably from 1 to 1.02, in particular 1, mole of ammonia per mole of phthalic anhydride, under atmospheric or superatmospheric pressure, advantageously at from 135° to 300° C., preferably from 200° to 280° C., especially from 240° to 270° C. It is possible to use pure phthalic anhydride but, in industrial operation, it is simpler and more economical to use technical-grade crude phthalic anhydride, for example of 90–95 percent by weight purity, as obtained, for example, by catalytic oxidation of naphthalene or o-xylene with air. Equally, the ammonia may be pure or mixed with inert gases, for example nitrogen or carbon dioxide. In general, phthalic anhydride is introduced as a melt, at a flow velocity of from 0.005 to 15, preferably from 0.1 to 1, meter/second into the mixing apparatus, whilst ammonia is introduced at a flow velocity of from 0.1 to 50, preferably from 1 to 15, meter/second. The phthalic anhydride advantageously is passed into the mixing apparatus at a temperature of from 135° to 300° C., preferably from 240° to 270° C., and the ammonia is passed into the mixing apparatus at from 50° to 300° C., preferably from 240° to 280° C., and under a pressure of from 1 to 50 bar, preferably from 2 to 10 bar. Ammonia can be introduced via a regulating device at one or more points of the mixing apparatus.

In a preferred embodiment of process step (a), the starting components are thoroughly mixed in a mixing apparatus, preferably by turbulent mixing of phthalic anhydride and ammonia in ejectors, each reactant entering the ejectors at the flow velocities stated above. If other mixing apparatuses are used, they are advantageously set so that the mixing velocity corresponds to that of the ejectors referred to above. This setting of the mixing velocity according to the invention can easily be defined by experiments in comparison with the mixing effect achieved in ejectors. Provided the stated mixing conditions are employed, a broad range of conventional stirring equipment may be used, namely injectors, ball jets, vortex jets, turbine stirrers, mixing nozzles, Lechler mixing nozzles, spiral turbines, planetary stirrers, centrifugal gyratory stirrers, rotating atomizers, internal tubular mixers with spirally arranged, adjustable deflector plates or packings, and impeller stirrers; impeller stirrers, multi-stream ejectors, internal tubular mixers and mixing nozzles are preferred. It is also possible to use apparatus and equipment which permits intensive mixing, eg. flow tubes, pipeline tees, airlift type stirrers, homogenizers, gyratory mixers, turbomixers, flow mixers, jet scrubbers, liquid-jet compressors and ejector-type tubular reactors. The residence time in the mixing apparatus is from 0.001 to 60, preferably from 0.01 to 10, seconds, the pressure is advantageously from 1 to 50, preferably from 2 to 10, bar, and the mixing temperature, which results from heating and/or directly from the temperature of the starting materials which enter the apparatus, is advantageously from 135° to 300° C., preferably from 200° to 280° C., especially from 240° to 270° C. The greater part, preferably from 50 to 80 percent by weight, of the phthalic anhydride is advantageously reacted in stage (a), ie. in the mixing apparatus.

From the mixing apparatus, the reaction mixture passes into the reactor (stage (b)), which consists of a heated reaction tube, and from there, having reacted, it passes to the working-up stage. In a preferred embodiment, the reaction tube can contain means to increase the mixing effect, for example packings, deflector plates or internal tubular mixers. Advantageously, a high flow velocity of the reaction mixture in stage (b) is used, by employing a narrow cross-section of the reaction tube and using approriate conveying pumps. The latter can be, for example, jet pumps, rotary pumps, rotary piston pumps, Roots pumps, screw pumps, eccentric pumps, vane pumps, centrifugal pumps, axial pumps or propeller pumps. In a preferred embodiment of the process, the flow velocities are determined by the cross-section and length of the reaction tube. Advantageously, flow velocities of from 0.01 to 50, especially from 0.1 to 15, meters/second are employed, with, for example, reactor cross-sections of from 10 to 200,000 mm², and tube lengths of from 0.1 to 100, preferably from 1 to 30, meters. At these velocities, the starting material is as a rule completely converted in stage (b) in a residence time of from 0.1 to 600, preferably from 1 to 30, seconds. The reaction in stage (b) is carried out at from 235° to 300° C., preferably from 240° to 280° C., especially from 245° to 270° C., under atmospheric or superatmospheric pressure, advantageously at from 1 to 50 bar, preferably from 2 to 10 bar.

At the end of the reactor, the reaction mixture, substantially consisting of phthalimide, is taken off as a melt, cooled, for example on a cooling drum or a cooled belt, and, advantageously, isolated as flake. In a preferred embodiment of the process, the mixture issuing from the reactor is absorbed, without intermediate isolation, in dilute sodium hydroxide solution. This gives a solution of sodium phthalamate which can be converted directly, without further purification, to anthranilic acid or isatoic anhydride.

The phthalimide prepared by the process according to the invention is a valuable starting material for the preparation of dyes, pesticides and pigments, especially copper phthalocyanines. It also serves as a stabilizer in aircraft fuel. Regarding the use of the material, reference may be made to Ullmanns Encyklopädie der technischen Chemie, Volume 13, page 735.

In the Examples which follow, parts are by weight and bear the same relation to parts by volume as that of the kilogram to the liter.

EXAMPLE 1

400 parts per hour of phthalic anhydride at 260° C. are fed, from a heated stock vessel, by means of a heated centrifugal pump, to an ejector of 0.21 meter/second. A reaction tube having an internal diameter of 25 millimeters and provided with a heating jacket is connected to the mixing nozzle, the tube being in the shape of a coil. The total length of the reactor is 30 meters. 46 parts of ammonia at 5.75 meters/second are injected hourly, at 260° C. under a pressure of 4 bar, into the ejector via a line provided with a heating jacket. In the ejector, the temperature is 260° C., the pressure 3.5 bar and the residence time 0.07 second. The exothermic phthalimide formation reaction commences immediately and is completed in a downstream reactor. In the latter, the temperature is 265° C., the pressure 3.5 bar, the residence time 2.05 seconds and the flow velocity 14.7 meters/second. After the mixture has travelled through 10 meters of reaction tube, the conversion is already in excess of 99 percent. The liquid end product is separated from the gaseous/vaporous constituents of the reaction mixture in a receiver, and 316 parts per hour of phthalimide, of melting point 233.4° C., are obtained, in addition to 0.4 percent of phthalic anhydride. The off-gas which leaves the receiver and which contains steam, phthalimide vapor, 0.4 percent by weight of ammonia and 0.4 percent by weight of phthalic anhydride, is absorbed in water, and the phthalimide which precipitates is isolated. Per hour, 79 parts of 99.6 percent by weight pure phthalimide are obtained, the remaining 0.4 percent by weight being phthalic anhydride; accordingly, a total of 395 parts per hour of phthalimide is obtained, corresponding to 99.4% of theory. The space-time yield is 27 parts per hour per liter of reactor. The throughput is 806,000 parts per hour per square meter of reactor cross-section. The phthalimide can be directly processed further, in the form in which it is obtained. The process can be carried out continuously, without pipe-line blockages occurring.

EXAMPLE 2

Similarly to Example 1, 715 parts of phthalic anhydride per hour are fed, at 260° C. and 0.37 meter/second, to an ejector to which a jacket-heated reaction tube of 100 mm internal diameter is connected. The tube is filled with packing over a length of 8 meters. The total length of the reactor is 10 meters. 82.5 parts per hour of ammonia at 260° C. and a pressure of 6 bar are introduced into the ejector at 7.83 meters/second. In the ejector, the temperature is 260° C., the pressure 4.95 bar and the residence time 0.05 second. In the reactor, the temperature is 265° C., the pressure 4.95 bar, the residence time 7.8 seconds and the flow velocity 1.27 meters per second. Following a procedure similar to Example 1, 567 parts per hour of phthalimide (melting point 233.5° C.) are obtained with a purity of 99.8 percent, the remaining 0.2 percent being phthalic anhydride. The off-gas leaving the receiver consists of steam, phthalimide vapor, 0.2 percent by weight of ammonia and 0.2 percent by weight of phthalic anhydride. From it, 142 parts per hour of phthalimide of 99.8 percent purity are obtained, the remaining 0.2 percent being phthalic anhydride. Accordingly, the total yield is 709 parts per hour of phthalimide, corresponding to 99.8% of theory. The space-time yield is 9 parts per hour per liter of reactor. The throughput is 90,000 parts per hour per square meter of reactor cross-section.

EXAMPLE 3

The mixture leaving the reactor after subjecting a mixture of 715 parts of phthalic anhydride and 82.5 parts of ammonia to the procedure described in Example 2 is dissolved in a mixture of 2,500 parts of 25 percent strength by weight sodium hydroxide solution, 5,700 parts of water and 22 parts of a 30 percent strength by weight aqueous solution of sodium sulfamate, and the resulting solution is continuously reacted with 2,525 parts of aqueous sodium hypochlorite solution (containing 13.8 percent by weight of active chlorine and 348 parts of sodium hypochlorite). Per hour, 640 parts of anthranilic acid (97% of theory), which is 99.9 percent pure and has a melting point of 141.1° C., are obtained.

We claim:

1. A concurrent, two stage process for the continuous preparation of phthalimide wherein phthalic anhydride and ammonia are reacted in stoichiometric ratios, which comprises:
(a) turbulently mixing phthalic anhydride and ammonia, in the ratios of 1.0 to 1.1 miles of ammonia per mole of phthalic anhydride, in turbulent mixing apparatus, wherein the degree of mixing is at least equivalent to that achieved by continuously passing both molten phthalic anhydride at a flow velocity of from 0.005 to 15 meters per second and ammonia at a flow velocity of from 0.1 to 50 meters per second into ejector mixers, the temperature in said mixing apparatus being from 135° to 300° C., the pressure within said mixing apparatus being from 1 to 50 bar, the ratio of ammonia to phthalic anhydride being 1 to 1.1 mole of ammonia per mole of phthalic anhydride, said phthalic anhydride and ammonia being both thoroughly mixed in said apparatus and reacted to the extent that from about 50 to 80% by weight of the phthalic anhydride is reacted within the mixing apparatus; and thereafter
(b) passing the reaction mixture from the mixing apparatus into and through a reaction tube at a flow velocity of from 0.01 to 100 meters per second, the temperature within said reaction tube being from 235° to 300° C. and the pressure within said reaction tube being from 1 to 50 bar, the reaction between the phthalic anhydride and the ammonia being completed within the reaction tube in a residence time of 0.1 to 600 seconds.

2. The process of claim 1, wherein the reaction is carried out with from 1 to 1.02 moles of ammonia per mole of phthalic anhydride.

3. The process of claim 1 or 2, wherein the reaction in step (a) is carried out from 200° to 280° C.

4. The process of claim 1 or 2, wherein the reaction in step (b) is carried out at from 240° to 280° C.

5. The process of claim 1, wherein the reaction in step (b) is carried out at a flow velocity of from 0.01 to 50 meter/second.

6. The process of claim 1, wherein the reaction in step (b) is carried out in a reactor with a cross-section of from 10 to 200,000 mm$^2$ and a tube length of from 0.1 to 100 meters.

7. The process of claim 1 wherein the products of reaction are directly absorbed in an alkali solution.

8. The process of claim 1 wherein the phthalic anhydride and ammonia reactants are introduced into said mixing stage in the mole ratio of 1.0 mole of ammonia per mole of phthalic anhydride.

9. The process of claim 1 wherein the mixing in step (a) is accomplished using ejector mixers.

10. The process of claim 1, wherein the reactor throughput is in excess of 10,000 kg/hr per square meter of reactor cross section.

11. The process of claim 9 wherein the phthalic anhydride and ammonia reactants are introduced into said mixing stage in the mole ratio of 1.0 mole of ammonia per mole of phthalic anhydride.

* * * * *